US012751846B2

(12) United States Patent
Helder

(10) Patent No.: US 12,751,846 B2
(45) Date of Patent: Oct. 6, 2026

(54) AORTIC ARCH REPAIR SYSTEMS, DEVICES AND METHODS

(71) Applicant: Octin Health, Inc., Minneapolis, MN (US)

(72) Inventor: Meghana Ram Kunkala Helder, Minneapolis, MN (US)

(73) Assignee: Octin Health, Inc., Minneapolis, MN (US)

(*) Notice: Subject to any disclaimer, the term of this patent is extended or adjusted under 35 U.S.C. 154(b) by 0 days.

(21) Appl. No.: 19/353,496

(22) Filed: Oct. 8, 2025

(65) Prior Publication Data

US 2026/0033969 A1 Feb. 5, 2026

Related U.S. Application Data

(63) Continuation of application No. PCT/US2025/012391, filed on Jan. 21, 2025.

(60) Provisional application No. 63/625,576, filed on Jan. 26, 2024.

(51) Int. Cl.

| | |
|---|---|
| ***A61F 2/958*** | (2013.01) |
| ***A61F 2/06*** | (2013.01) |
| ***A61M 25/10*** | (2013.01) |
| ***A61M 60/13*** | (2021.01) |
| ***A61M 60/38*** | (2021.01) |

(52) U.S. Cl.

CPC ............ *A61F 2/958* (2013.01); *A61M 60/13* (2021.01); *A61M 60/38* (2021.01); *A61F 2002/065* (2013.01); *A61M 2025/1052* (2013.01)

(58) Field of Classification Search

CPC A61F 2/958; A61M 60/13; A61M 2025/1052
See application file for complete search history.

(56) References Cited

U.S. PATENT DOCUMENTS

| | | | |
|---|---|---|---|
| 2001/0020160 | A1 | 9/2001 | Esch et al. |
| 2016/0022409 | A1 | 1/2016 | Aharon et al. |

(Continued)

FOREIGN PATENT DOCUMENTS

| | | | |
|---|---|---|---|
| CN | 111281463 | A | 6/2020 |
| WO | 2006136379 | A1 | 12/2006 |

(Continued)

OTHER PUBLICATIONS

International Search Report and Written Opinion mailed May 16, 2025, International Application No. PCT/US2025/012391, 35 pages.,.

*Primary Examiner* — Christopher D. Prone
(74) *Attorney, Agent, or Firm* — Fortem IP LLP

(57) ABSTRACT

System, devices and methods for providing a blood-free operative region for aortic arch repair procedures. Various embodiments disclose occlusion of the descending aorta, the innominate artery, the left carotid artery and the left subclavian artery while also providing sufficient perfusion distal of the occluding balloons. Various embodiments disclose performing aortic arch repair procedures while the patient's body temperature is maintained an normothermia (about 36 degrees C to about 37.5 degrees C). Other embodiments disclose performing aortic arch repair procedures while the patient's body temperature is maintained at slight hypothermia (about 30 degrees C to about 34 degrees C).

11 Claims, 9 Drawing Sheets

(56) References Cited

U.S. PATENT DOCUMENTS

2022/0305184 A1 9/2022 Yildiz et al.
2023/0211130 A1 7/2023 Lim

FOREIGN PATENT DOCUMENTS

WO WO-2023215303 A1 * 11/2023 ............ A61M 60/35
WO 2025160059 A1 7/2025

* cited by examiner

AORTIC ARCH REPAIR SYSTEMS, DEVICES AND METHODS

CROSS-REFERENCE TO RELATED APPLICATION(S)

This application is a continuation of International Patent Application No. PCT/US25/12391, field Jan. 21, 2025, which claims the benefit of priority to 63/625,576, filed Jan. 26, 2024, each of which is incorporated by reference herein in its entirety.

STATEMENT REGARDING FEDERALLY SPONSORED RESEARCH FOR DEVELOPMENT

None

FIELD OF THE INVENTION

The invention relates to systems, devices and methods for operating on the aortic arch.

BACKGROUND OF THE INVENTION

The aorta is the biggest artery in the body and begins above the aortic valve as the aortic root. It continues as the ascending aorta and then the arch as it gives rise to three vessels that give blood supply to the brain and arms. The aorta then proceeds down the thoracic cavity as the descending aorta and then transitions to become the abdominal aorta before splitting into the iliac arteries. Portions of the ascending and descending aorta are illustrated in the Figures as is the aortic arch. The aorta can become aneurysmal or enlarged at any of these points. An aneurysm is a life-threatening disease because the aortic walls, as the diameter of the aorta becomes increased, are made thinner and weaker. There is an aortic diameter at which the risk of aortic rupture (which differs for each individual patient) is deemed inevitable. Because of this risk, several cardiovascular surgical societies have recommended replacement of the ascending aorta and aortic arch at 5.0 cm in diameter. Besides aortic rupture, another fatal complication of an aortic aneurysm is an aortic dissection. This is where blood flows into the wall layers of the aorta through an intimal tear instead of blood flowing in the true lumen of the aorta. An aortic dissection can cause a heart attack, a stroke, kidney failure and leg and arm ischemia based on where the dissection exists. Both rupture and dissection have incredibly high mortality rates, up to 80%, if untreated.

Currently, the standard of care is prevention of aortic rupture or dissection by replacing the aneurysmal portions of the aorta preemptively, at approximately 5.0 cm. These aortic arch operations are high risk and carry a combined mortality and morbidity rate of 25% in the Society of Thoracic Surgeons National Database. Current operations to replace any portion of the aortic arch require what is called circulatory arrest.

Circulatory arrest is where all blood flow is stopped to provide a clear surgical field. To allow for circulatory arrest, a patient is cooled on the cardiopulmonary bypass machine to 18-24 C to reduce metabolic demand and then perfusion to the body and brain is removed completely resulting in ischemic times of approximately 30-90 minutes. In addition, the act of cooling and rewarming the body requires 4-5 hours of extra cardiopulmonary bypass time that would otherwise not be necessary.

It would be advantageous to provide a system, device and/or method that would obviate the need for circulatory arrest, provide blood flow to body and the brain, and eliminate the need for cooling and warming the patient reducing cardiopulmonary bypass times.

Various embodiments of the present invention address the issues, among others, discussed above.

BRIEF DESCRIPTION OF THE DRAWINGS

These drawings are exemplary illustrations of certain embodiments and, as such, are not intended to limit the disclosure.

DETAILED DESCRIPTION

Figure 1A:
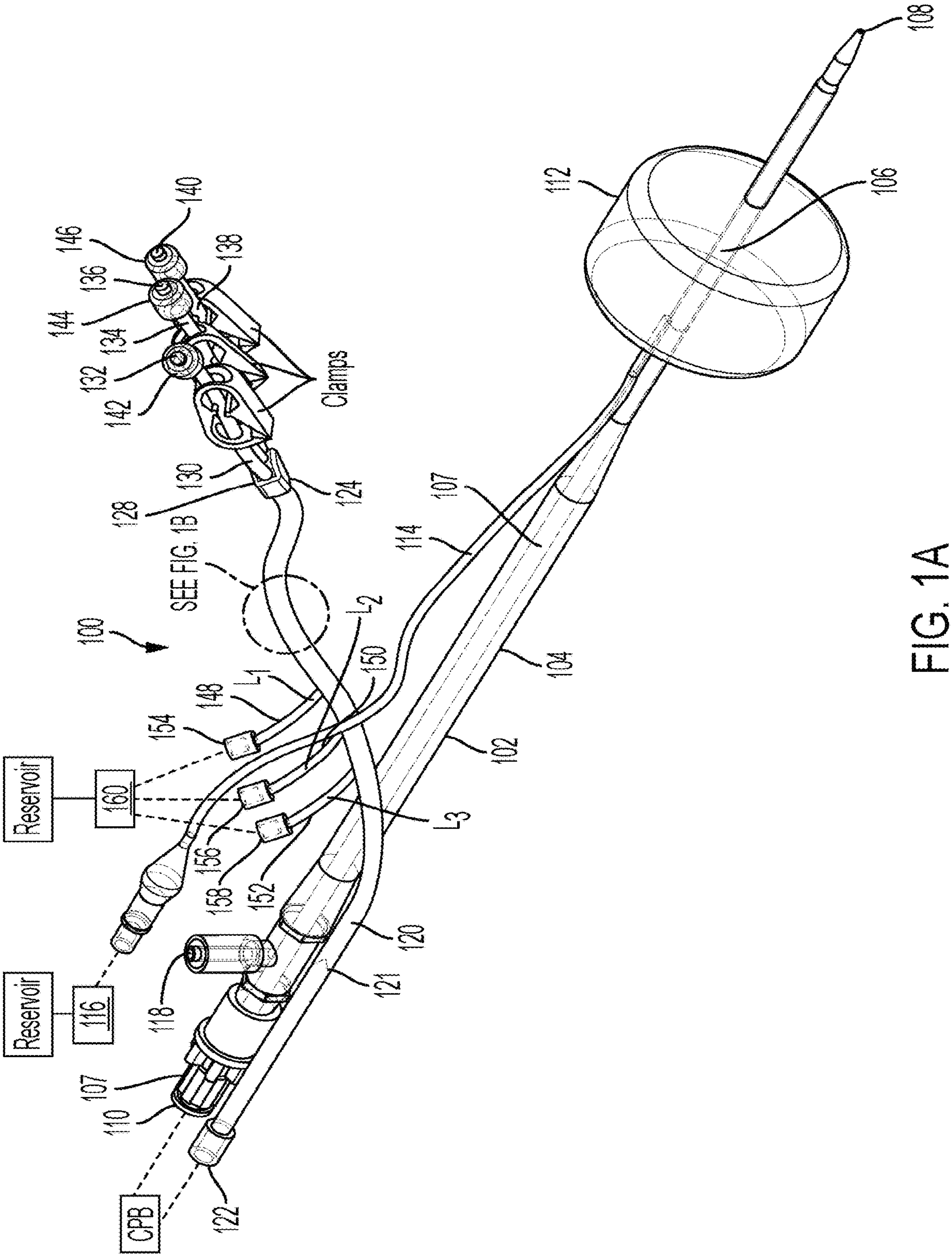
FIG. 1A illustrates a perspective partial cutaway view of one embodiment of the present disclosure.

Generally, and with reference to the Figures, the various disclosed embodiments may each include a main catheter or cannula 102 tube that is configured to be positioned across the aortic arch and into the descending aorta to provide sufficient blood flow to the lower body to meet metabolic needs at operative bodily temperatures at normothermia (about 36 to 37.5 C) or slight hypothermia (about 30 to 34 C). A range of bodily temperatures may be maintained during the disclosed operative methods, ranging from about 29 degrees C to about 37.5 degrees C. The main cannula 102 may comprise a 16 Fr (5.3 mm)-18 Fr (6.5 mm) cannula 102, though other sizes may also be employed. At, or just proximal to, the distal end or tip of the cannula tube 102, there may be an inflatable and deflatable descending aortic occlusion balloon 112 surrounding a distal region of the main cannula tube 102 which allows inflations (and deflations) of the balloon 112 to different normal aortic sizes (e.g., 26 mm-34 mm in diameter, though other sizes are within the scope of the present disclosure). The descending aortic balloon 112 may be 5-10 cm in length, though other lengths are within the scope of the present disclosure as will be well understood by the artisan.

There may be a de-airing portal 118 close to a connection point between a proximal end of the main cannula 102 and the cardiopulmonary bypass machine ("CPB") with one or more venous return lines V-line and one or more arterial lines A-line, wherein the arterial line(s) A-line(s) are in fluid communication with a main descending aorta lumen 106. Some embodiments may also include one or more lines configured to indicate the typical length of insertion point at which the proximal end of the descending aortic occlusion balloon 112 is confirmed to be distal to the left subclavian artery. This length may be based on researching typical aortic arch lengths on CT scans. Alternatively, the patient's specific aortic arch length may be measured via imaging or other techniques as well understood in the art.

Various embodiments described herein may also include one or more secondary cannula tubes 130, 134, 138 configured for insertion into the ostia of the arch vessels (innominate artery, left carotid artery and left subclavian artery) and, in combination with inflatable/deflatable secondary balloons 142, 144, 146, are configured to provide limited but sufficient blood flow at normothermia to the brain. Thus, each of the secondary cannula tubes 130, 134, 138 may each also be surrounded at or near a distal end of the secondary cannula tubes 130, 134, 138 by the inflatable and deflatable secondary balloons 142, 144, 146 that are, when inflated to the desired pressure, configured to occlude the internal lumens of the arch vessels ranging from a diameter of approximately 8 mm to 14 mm and approximately 0.5 cm to 1 cm in length. Other diameters and lengths are possible, each of which is within the scope of the present disclosure as will be readily understood by the skilled artisan.

In embodiments comprising two or more secondary cannula tubes, the two or more secondary cannula tubes, e.g., 130, 134, 138 may comprise separate inflation mechanisms that may be separately actuated to inflate or deflate the secondary cannula balloons 142, 144, 146 and comprise actuable clamps located proximal to the secondary cannula balloons 142, 144, 146 configured to restrict or allow blood flow through the relevant secondary cannula tube 130, 134, 138. Preferred embodiments comprise three secondary cannula tubes 130, 134, 138, and a single secondary cannula tube 130. The secondary cannula tubes 130, 134, 138 may comprise a common starting point branching away from one or more lumens defined by a main secondary cannula tube 120 disposed proximal to the secondary cannula tubes 130, 134, 138. This arrangement, inter alia, and as will be discussed further infra, allows provision of different, or the same, lengths for the secondary cannula tubes 130, 134, 138 which may be customized for individual patients or subgroups of patients, as well as offering the surgeon discretion regarding the order of inflation and deflation of the secondary cannula tubes 130, 134, 138 as well as customization of the inflation pressure magnitude(s) and related compliance of the inflated secondary cannula balloons 142, 144, 146.

In some embodiments, the balloons 112, 142, 144, and/or 146 may be independently inflated as described in further detail herein. In other embodiments, at least some of the balloons 112, 142, 144, 146 may inflated at the same time. For example, secondary balloons 142, 144, 146 may be inflated independently in some embodiments, while in other embodiments secondary balloons 142, 144, 146 may be inflated at the same time.

In some embodiments, the main secondary cannula tube may comprise a flow rate limiting valve 121 as is well known in the art and which may allow a maximum flow rate therethrough to limit the blood flowing to the patient's brain to prevent cerebral edema. The maximum flow rate may be within a range of about 750 cc/min to about 900 cc/min.

The main cannula tube 102 with associated and defined lumen 106 extends through the descending aortic occlusion balloon 112 such that blood flow is enabled through the tube 102 and distally away from a distal opening or end 108 of the main cannula tube 102 in an antegrade direction into the descending aorta. Similarly, the secondary cannula tubes 130, 134, 138 each define a lumen that extends through the associated secondary balloon 142, 144, 146 such that blood flow is enable through the secondary cannula tubes 130, 134, 138 and distally away from a distal opening or end of each secondary cannula tube 130, 134, 138 in an antegrade direction into the relevant aortic arch artery. The balloons in each case act to prevent a retrograde or backflow of blood when the balloons are sufficiently inflated.

The above is a generalized description of the various embodiments of the present disclosure. Specific structures of the various embodiments will be described in greater detail infra.

The structures used in the described operative embodiments will now be described in detail with reference to FIGS. 1A-6B. Each of the described embodiments of FIGS. 1A-5 comprises a system that includes a main catheter tube 102 component as shown in each of FIGS. 1A-5. FIGS. 6A and 6B illustrate a system 100' comprising a similar main catheter tube 102 with a slight variation in fluid flow management to the arch vessels.

Main Body Catheter

With reference to the Figures, each embodiment of the systems, devices and/or methods described herein comprises a main catheter tube 102 comprising a shaft or housing 104 defining a descending aortic lumen 106 therethrough extending from a proximal opening 110 to a distal opening 108. The main catheter tube 102 further comprises a descending aortic occlusion balloon 112 surrounding, and operatively attached to, a distal region of the main catheter tube 102 at a point that may be proximal to the distal opening 108. The descending aortic occlusion balloon 112 is in operative fluid communication with a main inflation tube 114 which is, in turn, operatively fluidly connected at a proximal end to a main inflation and deflation pump 116. The main pump 116 is configured to inflate and deflate the descending aortic occlusion balloon 112 via the main inflation tube 114 when the main catheter tube 102 and descending aortic occlusion balloon 112 have been properly positioned within the aorta.

As shown in the Figures, the main catheter 102 comprises a housing or shaft 104 that, in turn, defines the descending aortic lumen 106 extending through the length of the main catheter tube 102. The main catheter tube 102 is configured to extend through the associated descending aortic occlusion balloon 112 and, in some embodiments, to extend distally beyond the descending aortic occlusion balloon 112. The descending aortic lumen 106 is configured to allow a defined, and in some cases a limited but sufficient, amount of antegrade blood flow therethrough to the patient's body, while the inflated balloon 112 is configured to block retrograde blood flow. In some embodiments, a dilator 107 as is known in the art may be used to gently expand the access and which may be withdrawn prior to connecting the CPB machine with the main catheter tube 102 at a proximal end 110.

Figure 1B:
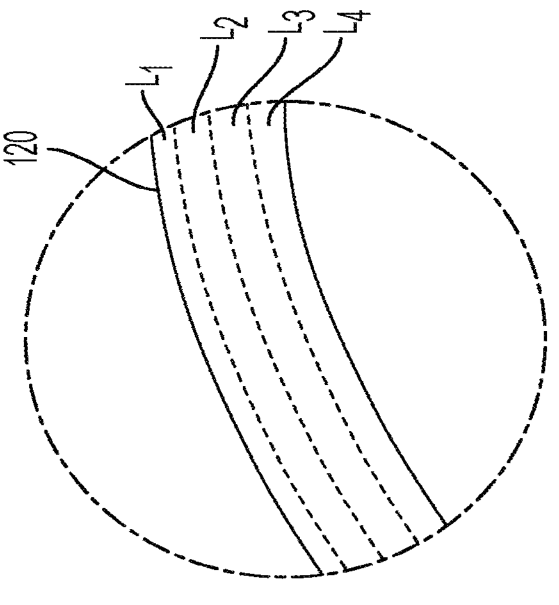
FIG. 1B illustrates an enlarged section of FIG. 1A.

A proximal end of the descending aortic lumen 106 may be placed in operative and fluid communication with an arterial line (A-line) of a CPB machine to allow blood flow from the CPB machine through the main catheter and into the patient's aorta at a position that is distal to the descending aortic occlusion balloon 112. A return venous line may be provided as shown in FIG. 1D.

The system 100 of FIG. 1A-1E further comprises a secondary cannula device comprising a main secondary cannula tube 120 with three branched secondary cannula tubes 130, 134, 138 that are operatively connected with the main secondary cannula tube 120 as will be discussed further below. The three branched secondary cannula tubes 130, 134, 138 are configured for insertion into individual ones of the ostia of the arch vessels (innominate artery, left carotid artery and left subclavian artery) for provision of blood flow to the patient's brain and upper body.

Embodiments of the system 100 may include the main secondary cannula 120 comprising a flow rate limiting valve 121 as is well known in the art. The flow rate limiting valve 121, when present, may be located within the main secondary cannula tube 120, which may allow a maximum flow rate therethrough to limit the blood flowing to the patient's brain to prevent cerebral edema. The maximum flow rate value allowed by the flow rate limiting valve 121 may be within a range of about 750 cc/min to about 900 cc/min.

Each of secondary cannula tubes 130, 134, 138 are illustrated as comprising a distal region that is surrounded by, and operatively attached to, inflatable and deflatable secondary balloons 142, 144, 146 which, when sufficiently inflated, are configured to occlude the internal lumens of the arch vessels and to prevent backflow of the blood when the compliant secondary balloons 142, 144, 146 are sufficiently inflated. The secondary cannulas 130, 134, 138 each define a lumen therethrough and extend through the secondary balloons 142, 144, 146 such that a distal end opening 132, 136, 140 of the secondary cannulas 130, 134, 138 allows for blood flow in an antegrade direction into the relevant arch vessel at a point that is distal to the secondary balloons 142, 144, 146.

A manifold 128 or similar operative connection mechanism may be provided at a proximal end of each of the secondary cannulas 130, 134, 138 to transition fluid flow (both blood and inflation fluid) from the main secondary cannula tube 120 to the secondary cannulas 130, 134, 138. As shown, the proximal end 122 of the main secondary cannula tube 120 may be placed in operative and fluid communication with the CPB machine such that oxygenated blood flows away from the CPB machine through the main secondary cannula tube 120 toward the manifold 128. The distal end 124 of the main secondary cannula tube 120 is operatively connected with the manifold 128 which is configured to separate the incoming blood flow flowing into the manifold 128 such that the incoming blood flow is divided into blood flowing through the secondary cannulas 130, 134, 138. Clamps may be provided to restrict or allow blood flow through the secondary cannulas 130, 134, 138 as appropriate.

The secondary balloons 142, 144, 146 are in fluid and operative communication with an inflation and deflation pump 160. In a preferred embodiment, the pump 160 comprises a multiplexing capability such that the pump 160 is configured to independently inflate or deflate individual secondary balloons 142, 144, 146 and, in some embodiments, configured to inflate each secondary balloon 142, 144, 146 to a different inflation pressure and/or size (diameter) to provide effective occlusion of the subject arch vessel which may vary in diameter. As illustrated in FIGS. 1A and 1B, first, second and third secondary inflation tubes 148, 150, 152 are provided and comprise, respectively, proximal ends 154, 156, 158 that are in operative and fluid communication with pump 160. The opposing ends of the first, second and third secondary inflation tubes 148, 150, 152 are each in operative communication with, and may be merged within, the main secondary cannula 120. First, second and third inflation tubes 148, 150, 152 each define individual lumens L1, L2, L3.

As shown in FIG. 1B, the first lumen L1 continues from the first secondary inflation tube 148 and continues and is merged and/or defined within and along a portion of the main secondary cannula tube 120. In some embodiments, the first secondary inflation tube 148 is contained within the main secondary cannula tube 120.

Similarly, the second lumen L2, separated from the first lumen L1 also is defined within and along a portion of the main secondary cannula tube 120. In some embodiments, the second secondary inflation tube 150 may be contained within the main secondary cannula tube 120. The third lumen L3, separated from both the first lumen L1 and the second lumen L2, is also defined within and along a portion of the main secondary cannula tube 120. In some embodiments, the third secondary inflation tube 152 may be contained within the main secondary cannula tube 120.

The blood moving distally from the CPB machine through the secondary cannula 120 tube is configured to flow along a main secondary blood flow lumen L4 also defined within the main secondary cannula 120 and that is separated from the inflation lumens L1-L3 and/or the first, second and third secondary cannulas 148, 150, 152 within the main secondary cannula 120, wherein the main secondary blood flow lumen L4 continues to an operative and fluid communication with the manifold 128.

Each of the first, second and third lumens L1, L2 and L3, and in some embodiments the first, second and third secondary inflation tubes 148, 150, 152, extend distally to the manifold 128 which provides operative and fluid communication between the first lumen L1 and the first secondary balloon 142, the second lumen L2 and the second secondary balloon 144, and the third lumen L3 and the third secondary balloon 146 such that the individual secondary balloons 142, 144, 146 may be individually inflated and deflated as described above using pump 160.

Figure 1C:
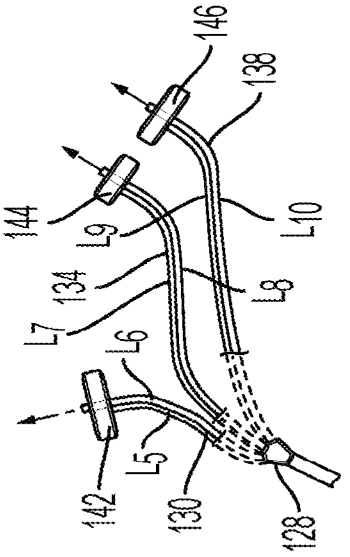
FIG. 1C illustrates a side cutaway view of the embodiment of FIG. 1A.
Figure 1D:
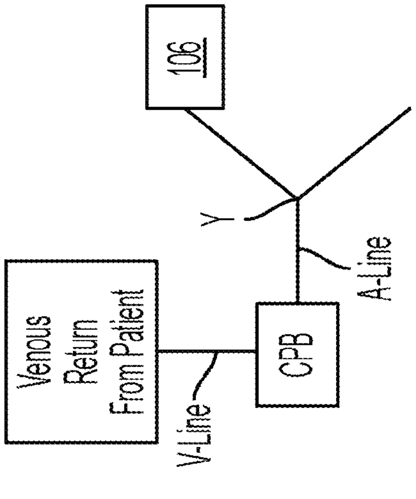
FIG. 1D illustrates a schematic view of one embodiment of a cardiopulmonary bypass machine and related lines.

As shown in FIG. 1C, the first, second and third secondary cannulas tubes 130, 134, 138 are each divided into two lumens. A first lumen in each secondary cannula tube 130, 134, 138 is in fluid communication with the inflation and deflation pump 160 for inflating and deflating the relevant secondary balloon. The second lumen in each secondary cannula tube 130, 134, 138 is in fluid communication with the CPB and the fourth lumen L4 and configured for provision of blood flow in an antegrade direction and extends through, and terminates distal to, the relevant secondary balloon 142, 144, 146. The manifold 128 is configured to separate the incoming (or departing) infusion fluid and the incoming blood flow into individual lumens defined within the three separated secondary cannulas 130, 134, 138 tubes.

Thus, the first secondary cannula tube 130 may be divided into a first secondary inflation lumen L5 which is in fluid communication with the interior of the first secondary balloon 142, and first secondary perfusion lumen L6 which, as described above, extends through, and distally past, the first secondary balloon 142 to provide antegrade blood flow to the brain and upper body. Similarly, the second secondary cannula tube 134 may be divided into a second secondary inflation lumen L7 and a second secondary perfusion lumen L8 that extends through and terminates distal to the second secondary balloon 144. Finally, secondary cannula tube 138 may be divided into a third secondary inflation lumen L9 and a third secondary perfusion lumen LIO that extends through the third secondary balloon 146 and terminates distal to the third secondary balloon 146. In each case, the secondary cannula tube 130, 134, 138 comprises a distal end 132, 16, 140 wherein the distal portion of the secondary cannula tube 130, 134, 138 that forms or defines the blood flow lumen L6, L8, LIO extends distally beyond the portion of the secondary cannula tube that forms or defines the inflation flow lumen.

The secondary cannula device embodiments may comprise one, two or three secondary inflation paths.

Accordingly, the first secondary inflation path may comprise an inflation or deflation device, e.g. a pump 160 which is in fluid communication with the first inflation lumen L1 which extends distally to the manifold 128. The manifold 128 is configured to fluidly communicate and connect the first inflation lumen L1 with the first secondary inflation lumen L5 which, in turn, is in fluid communication with an interior of the first secondary balloon 142.

Accordingly, the first secondary inflation path may comprise an inflation or deflation device, e.g. a pump 160 which is in fluid communication with the first inflation lumen L1 which extends distally to the manifold 128. The manifold 128 is configured to fluidly communicate and connect the first inflation lumen L1 with the first secondary inflation lumen L5 which, in turn, is in fluid communication with an interior of the first secondary balloon 142.

Similarly, the second secondary inflation path may comprise an inflation or deflation device, e.g. a pump 160 which is in fluid communication with the second inflation lumen L2 which extends distally to the manifold 128. The manifold 128 is configured to fluidly communicate and connect the second inflation lumen L2 with the second secondary inflation lumen L7 which, in turn, is in fluid communication with an interior of the second secondary balloon 144.

The third secondary inflation path may comprise an inflation or deflation device, e.g. a pump 160 which is in fluid communication with the third inflation lumen L3 which extends distally to the manifold 128. The manifold 128 is configured to fluidly communicate and connect the third inflation lumen L3 with the second secondary inflation lumen L9 which, in turn, is in fluid communication with an interior of the third secondary balloon 146.

As will be readily apparent to the skilled artisan, in addition to an inflation pump (116 and/or 160), one or more syringes may be used to inflate and/or deflate one or more of the balloons 112, 142, 144, 146 discussed herein. What is required is a device configured to inflate and deflate each of the balloons 112, 142, 144, 146.

The secondary cannula device may also comprise one, two or three secondary blood flow paths.

A first secondary blood flow path may comprise the main secondary blood flow lumen L4 defined in the main secondary cannula 120 extending distally from the CPB to the manifold 128. The manifold is configured to communicate and connect the main flood flow lumen L4 with a first secondary blood flow lumen L6 defined by the first secondary cannula 130, wherein the antegrade blood is configured to flow distally away from the distal end of the first secondary cannula 130 and into a first arch vessel, e.g. the innominate artery.

A second secondary blood flow path may comprise the main secondary blood flow lumen L4 defined in the main secondary cannula 120 extending distally from the CPB to the manifold 128. The manifold is configured to communicate and connect the main flood flow lumen L4 with a second secondary blood flow lumen L8 defined by the second secondary cannula 134, wherein the antegrade blood is configured to flow distally away from the distal end of the second secondary cannula 134 and into a first arch vessel, e.g. the left carotid artery.

A third secondary blood flow path may comprise the main secondary blood flow lumen L4 defined in the main secondary cannula 120 extending distally from the CPB to the manifold 128. The manifold is configured to communicate and connect the main flood flow lumen L4 with a third secondary blood flow lumen LIO defined by the third secondary cannula 138, wherein the antegrade blood is configured to flow distally away from the distal end of the third secondary cannula 138 and into a third arch vessel, e.g. the left subclavian artery.

Figure 1F:
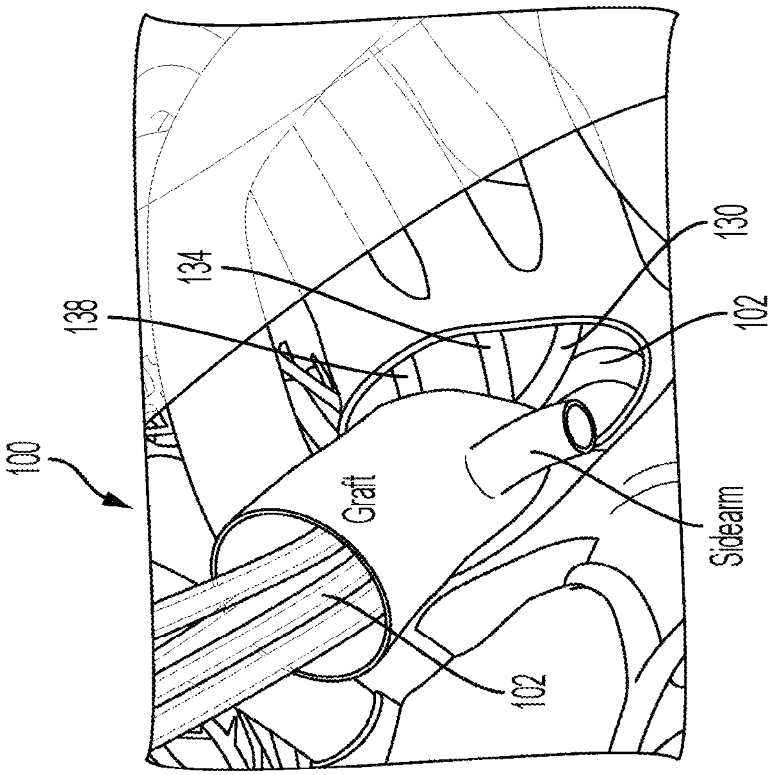
FIG. 1F illustrates a perspective view of one embodiment of the present disclosure.
Figure 1E:
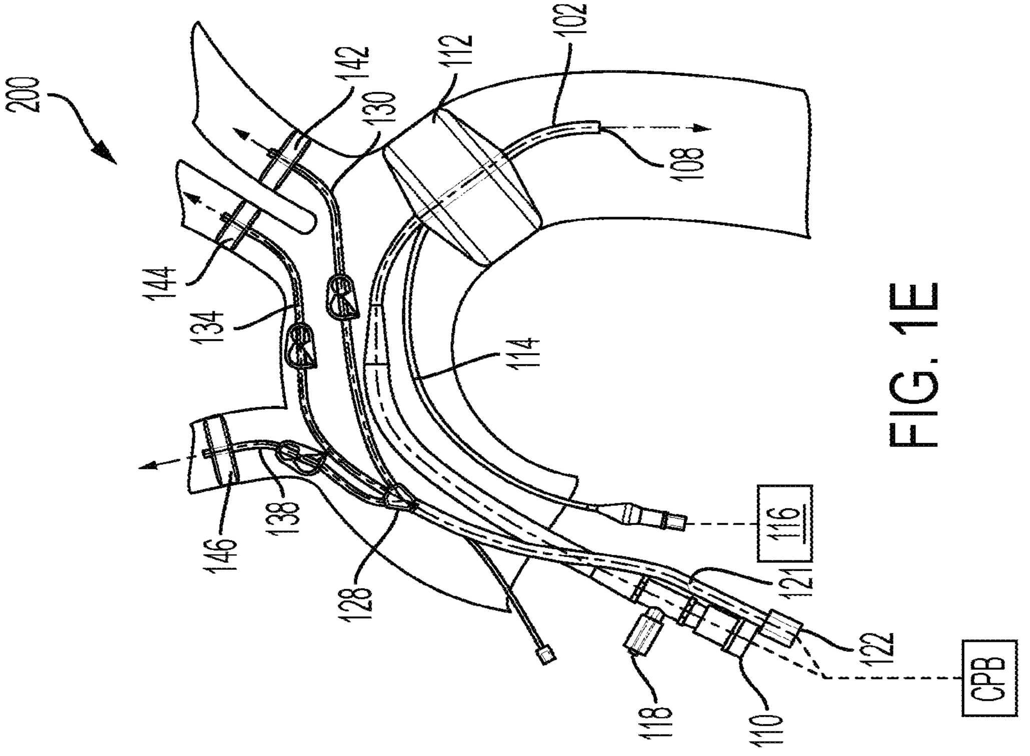
FIG. 1E illustrates a side partial cutaway view of the embodiment of FIG. 1A positioned within the vasculature.

FIG. 1E illustrates the system 100 described above in connection with FIGS. 1A-1C with the secondary cannula tubes 130, 134, 138 disposed within the respective ostias of the aortic arch vessels and wherein the secondary balloons 142, 144, 146 are at least partially inflated to occlude the vessels. In addition, the main descending aortic balloon 112 is shown as inflated within the descending aorta to occlude the descending aorta. Arrows indicate the antegrade blood flow direction through the secondary cannulas 130, 134, 138 into the respective arch vessels and through the main body cannula 102 into the descending aorta. As discussed, when the operative procedure is completed, the secondary balloons 142, 144, 146 and the main descending aortic balloon 112 may be deflated and the system 100 withdrawn from the patient.

FIG. 1F illustrates an exemplary hemi-arch graft in a position proximate with the previously preloaded graft being positioned slid along the main catheter tube 102 and over the secondary cannula device described above and comprising first, second and third secondary cannula tubs 130, 134, 138 as well as the main secondary cannula to a position that is in proximity with the resected aorta, in this scenario a hemi-arch resection, to allow the distal anastomosis to be completed. The illustrated graft comprises a substantially cylindrical hollow sleeve with two open ends and a branched sidearm defining a lumen that fluidly communicates with the interior of the graft's hollow cylindrical sleeve as is well known in the art.

The sleeve construction of the graft allows the surgeon to preload the graft by simply sliding the graft over a distal portion of the main cannula 102. Then, when the aortic arch is prepared, the graft may be slid in a distal direction over the main cannula 102 and the secondary cannula device in preparation for anastomosis. The exemplary graft of FIG. 1F may be used in combination with at least the system 100 described above.

With continued reference to FIGS. 1A-1E, FIGS. 2A-2C illustrate another embodiment comprising a system 200 comprising an embolic protection device operatively connected with each of the secondary cannula 130, 134, 138 and/or the secondary balloons 142, 144, 146 at a location distal to the secondary balloons 142, 144, 146. System 200 is the same as system 100, but with the addition of the embolic protection devices 202, 204, 206. The embolic protection devices 202, 204, 206 may comprise an illustrative, and without limitation, a metallic fine mesh cage or scaffold and, in some embodiments may be inflated and deflated, or expanded and contracted, either as a result of the secondary balloon expansion and contraction during inflation and deflation, or by a separate mechanism such as a self-expanding cage or scaffold. Other embolic protection devices will become apparent to the skilled artisan, each of which is within the scope of the present disclosure.

Figure 2B:
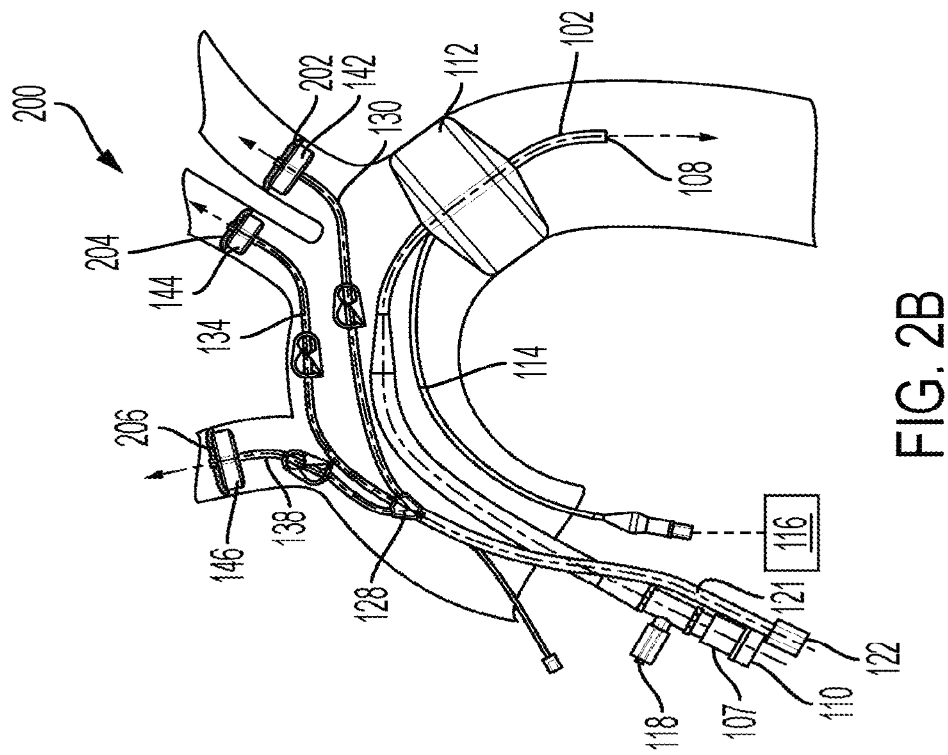
FIG. 2B illustrates a side and partial cutaway view of the embodiment of FIG. 2A positioned within the vasculature and including, inter alia, inflated secondary cannula balloons and related distal embolic protection devices.
Figure 2A:
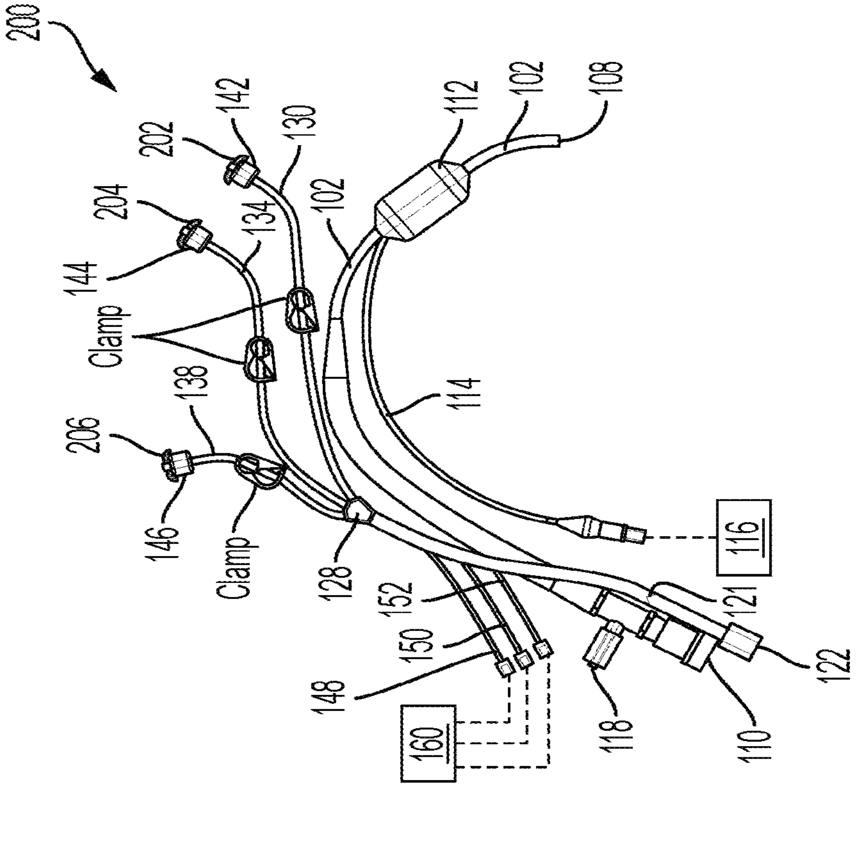
FIG. 2A illustrates a side and partial cutaway view of one embodiment of the present disclosure including, inter alia, secondary cannula balloons with distal embolic protection devices.

Thus, FIG. 2B shows the system 200 with all cannulas discussed in connection with FIGS. 1A-1E in position within the vasculature. The secondary balloons 142, 144, 146 are at least partially expanded and may expand to a position that is proximate to, but not touching, the relevant vessel wall as illustrated. Stated differently, a side surface of one or more of the secondary balloons 142, 144, 146 may be spaced apart from the vessel wall. In the illustrated embodiment comprises the embolic protection devices 202, 204, 206 expanded to be in contact with the vessel wall. In other embodiments, the secondary balloons 142, 144, 146 may be expanded to contact the vessel wall. In other embodiments, the embolic protection device(s) may be located on a proximal side of the secondary balloons 142, 144, 146. In other embodiments, the embolic protection device(s) may be located around a side surface of the secondary balloons 142, 144, 146.

Figure 2C:
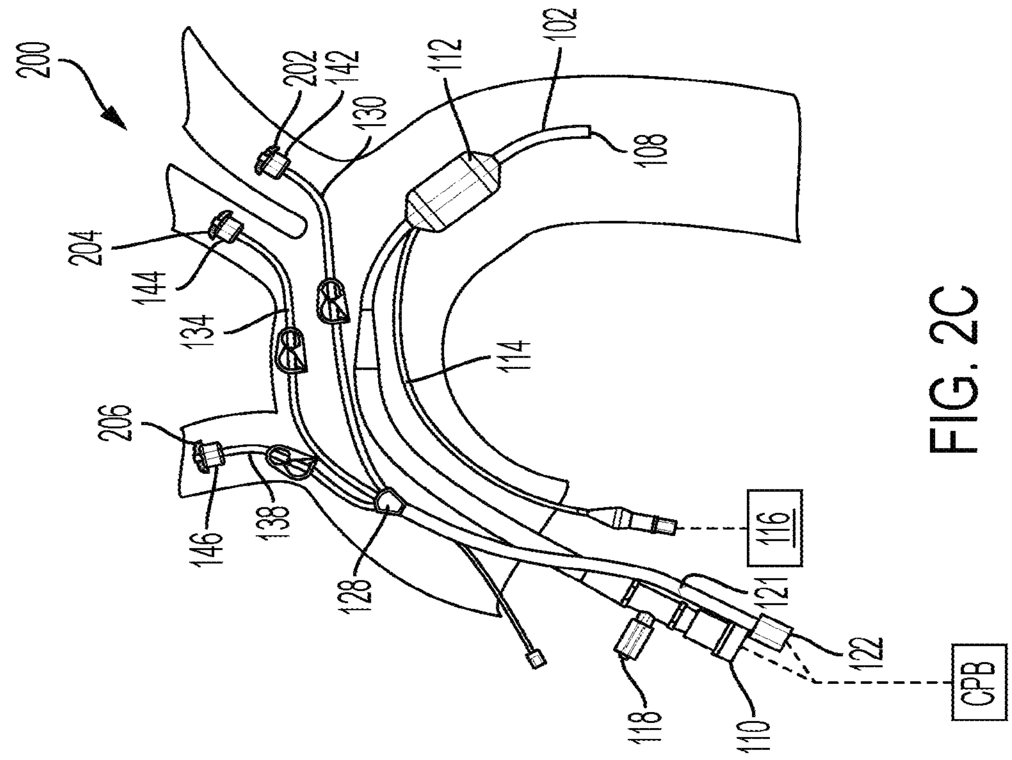
FIG. 2C illustrates a side and partial cutaway view of the embodiment of FIGS. 2A and 2B positioned within the vasculature and including, inter alia, deflated secondary cannula balloons and related distal embolic protection devices.

FIG. 2C shows system 200 in a configuration that results before or after expansion of the secondary balloons 142, 144, 146 and the associated embolic protection devices 202, 204, 206. Balloons 142, 144, 146 and the embolic protection devices 202, 204, 206 are in a deflated or contracted or compressed configuration to allow for ease of translation into and out of the vasculature.

The remainder of system 200 is the same as described in connection with FIGS. 1A-1E. System 200 may be used with a single secondary cannula tube and secondary balloon, or with more than one, e.g., three secondary cannula tubes 130, 134, 138 and associated secondary balloons 142, 144, 146.

Figure 3A:
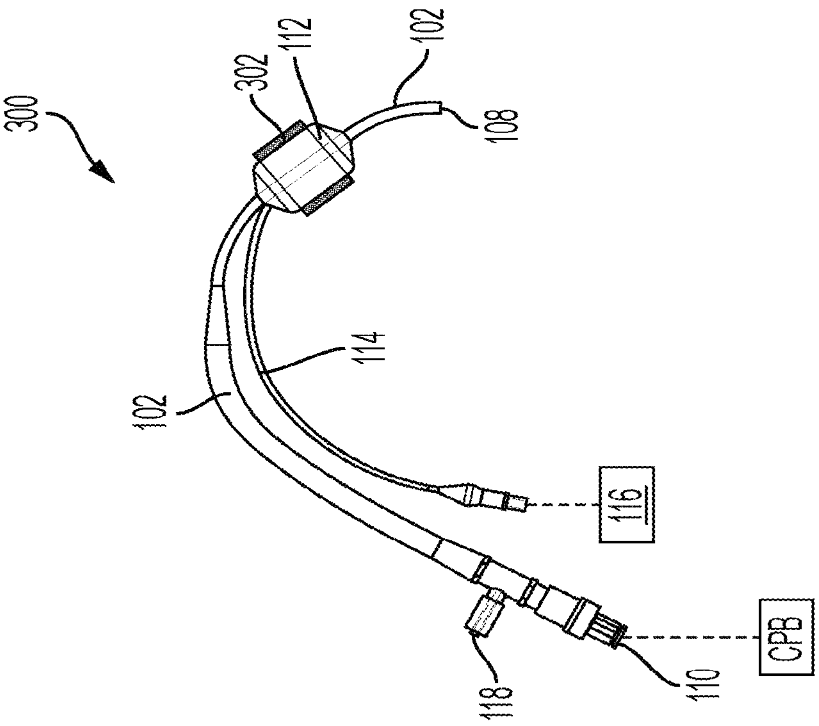
FIG. 3A illustrates a side and partial cutaway view of one embodiment of the present disclosure.
Figure 3C:
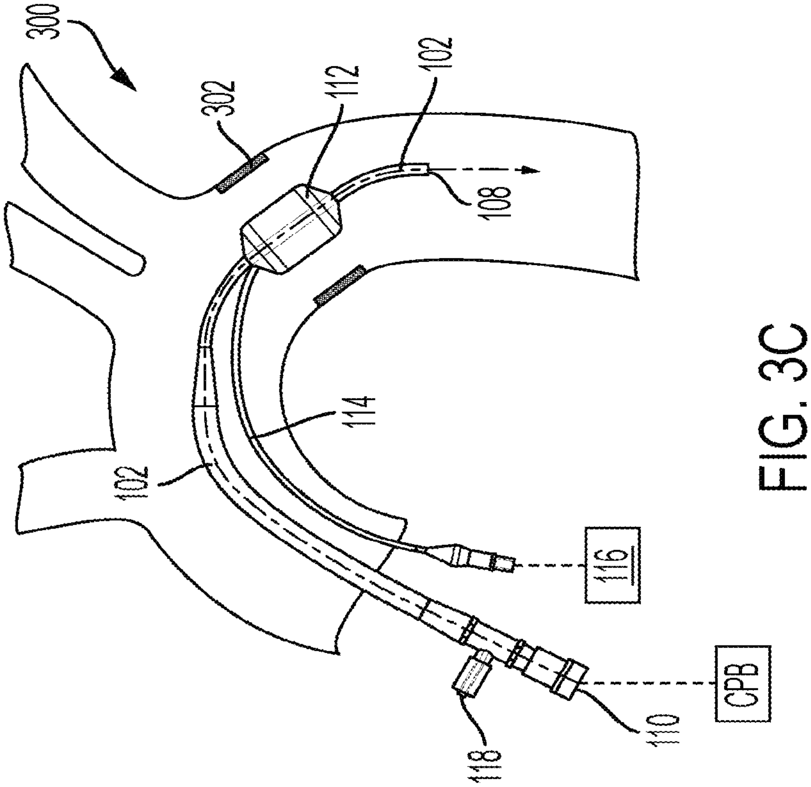
FIG. 3C illustrates a side and partial cutaway view of the embodiment of FIGS. 3B and 3B positioned within the relevant vasculature with, inter alia, a deflated balloon and implanted stent.
Figure 3B:
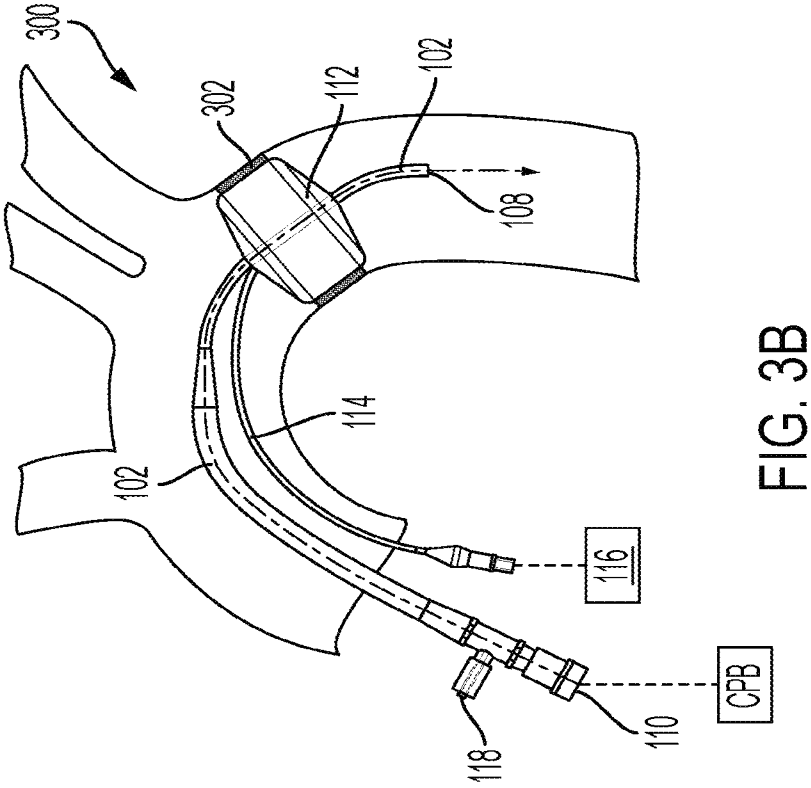
FIG. 3B illustrates a side and partial cutaway view of the embodiment of FIG. 3A positioned within the relevant vasculature with, inter alia, an inflated balloon with stent.

Turning now to FIGS. 3A-3C, another embodiment of a system 300 is illustrated that comprises the previously described embodiments of the main cannula or catheter tube 102. In this embodiment, the main body cannula or catheter tube 102 is used as a delivery device for a thoracic endovascular stent, also known as a frozen elephant trunk or frozen elephant trunk stent 302, an expandable stent device that is well known in the art. The thoracic endovascular, or frozen elephant trunk, stent 302 may, as shown, be preloaded on an at least partially deflated main descending aortic balloon 112 and configured to be translated distally with the balloon 112 for expanded deployment within the descending aorta as shown when the main descending aortic balloon 112 is positioned and inflated. The frozen elephant trunk stent 302 may be sized 10 cm in length and ranging from 26 to 34 mm in diameter and configured to expand into and against the descending aorta vessel walls for implantation or installation. Other sizes are within the scope of the present disclosure. The balloon 112 may then be deflated and the main cannula tube 102 withdrawn from the patient. This system 300 may be used alone, or in combination with systems 100 and 200 described above, or with system $00-400 which is discussed below.

Figure 5:
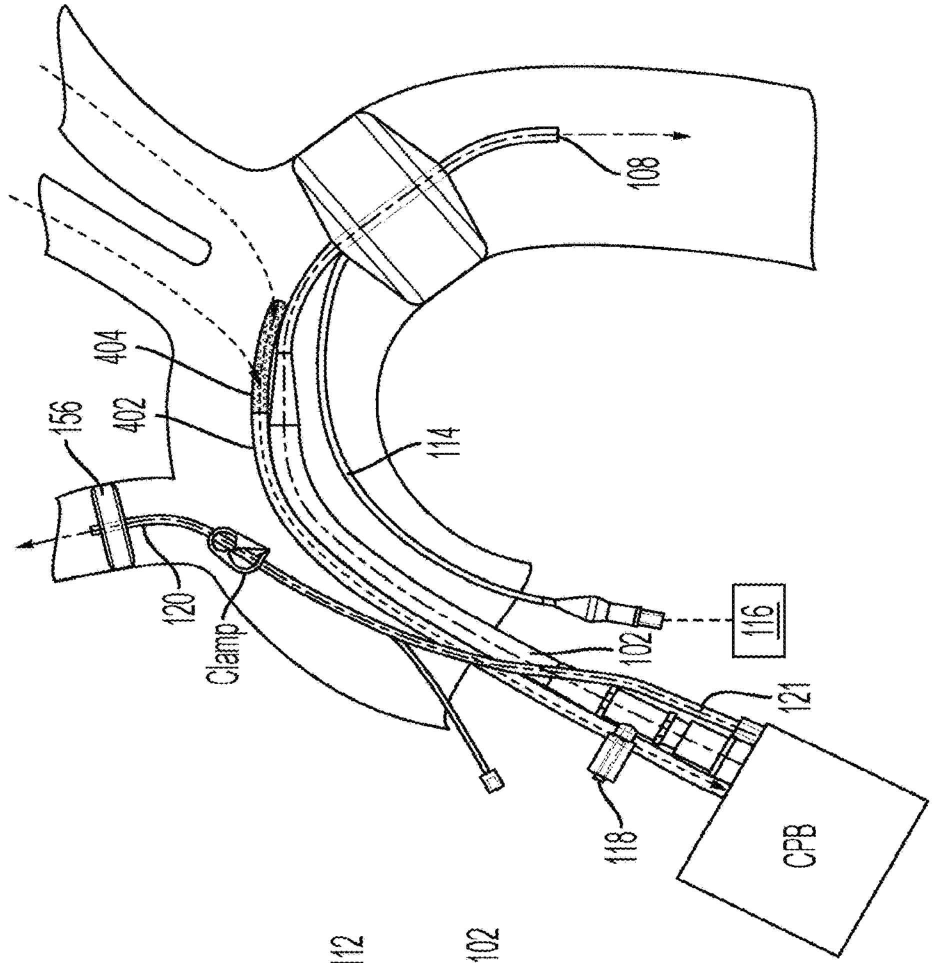
FIG. 5 illustrates a side and partial cutaway view of one embodiment of the present disclosure.
Figure 4:
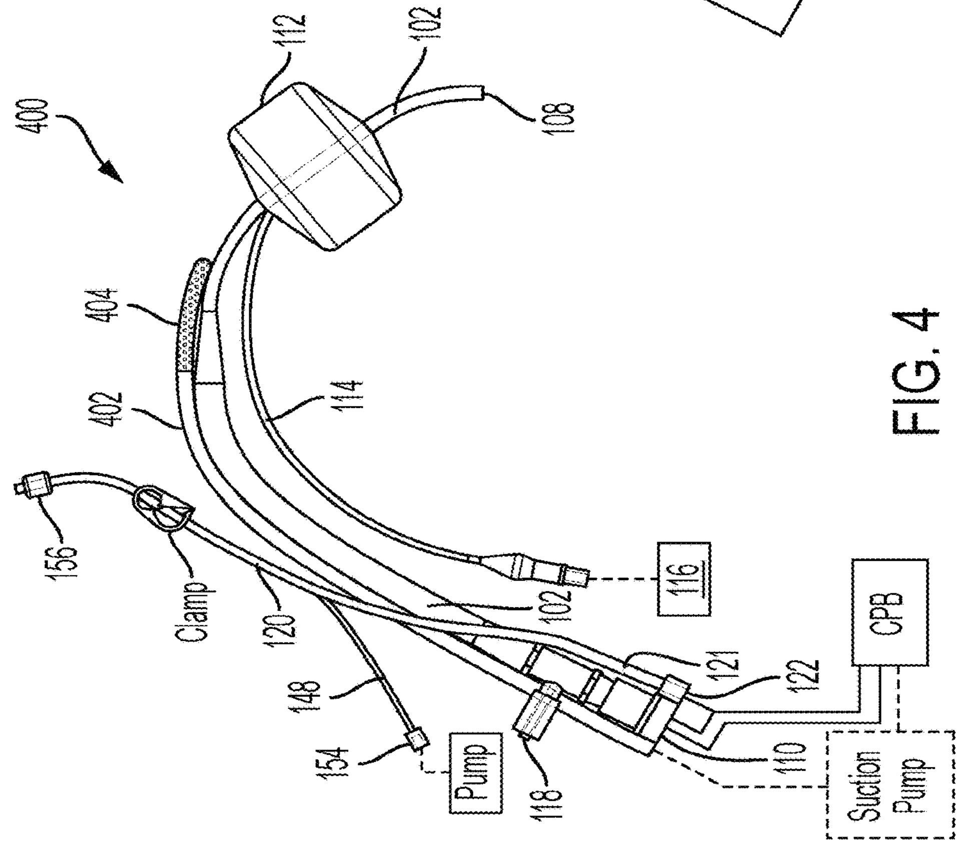
FIG. 4 illustrates a side and partial cutaway view of one embodiment of the present disclosure.
Figure 6A:
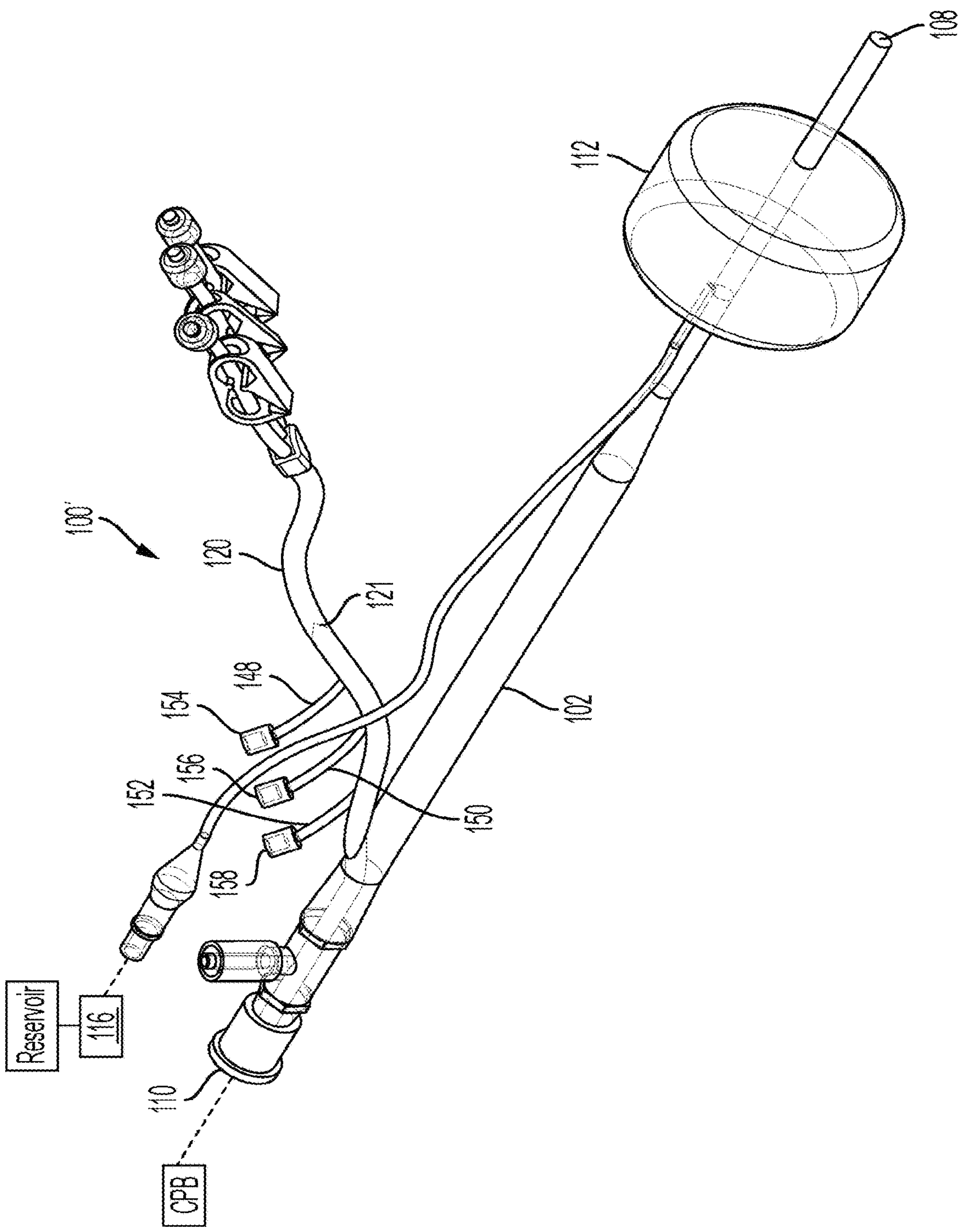
FIG. 6A illustrates a perspective and partial cutaway view of one embodiment of the present disclosure.
Figure 6B:
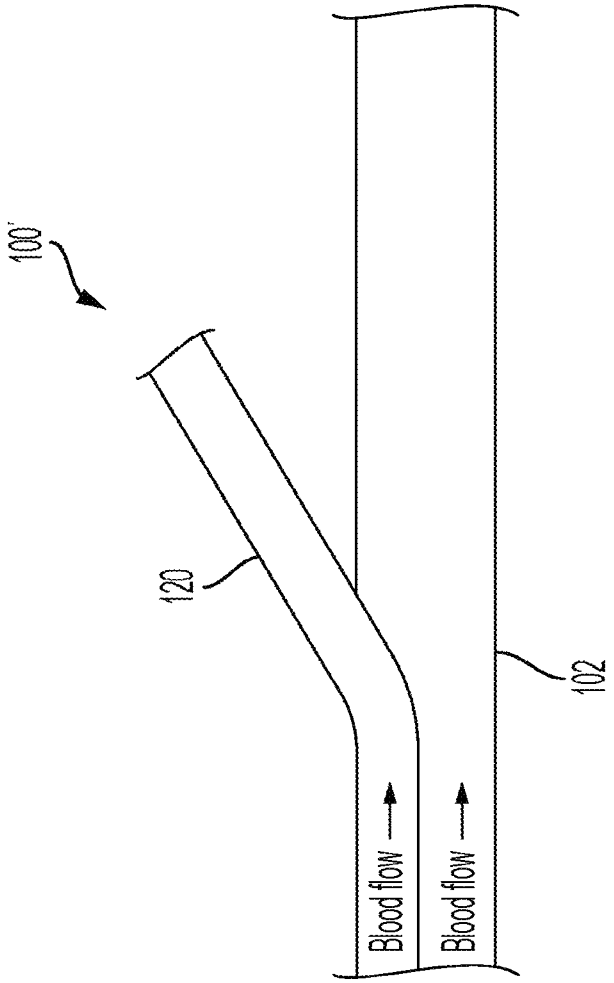
FIG. 6B illustrates a portion of the embodiment of FIG. 6A.

FIGS. 4 and 5 illustrate another embodiment of a system 400 comprising the embodiments of the main body cannula or catheter 102 as described above. In this embodiment, there is a main secondary cannula tube 120 as described above which is in fluid communication with an inflation and deflation pump via secondary inflation tube 148 and a proximal interconnection element 154 which secures an operative communication with the pump and the main secondary cannula tube 120 and an inflatable and deflatable secondary balloon 156 located at or near a distal end of the main secondary inflation tube 120 and which surrounds the main secondary inflation tube. In addition, the main secondary cannula tube 120 is in operative fluid communication at a proximal end 122 with the CPB machine as described above whereby blood is configured to flow distally through the secondary cannula 120 and distally away from the distal end of the secondary cannula 120 to provide perfusion to the brain. The main secondary cannula 120 extends through the, and terminates distal to, the secondary balloon 156 to allow blood flow from the CPB machine through the main secondary cannula and into a subject arch vessel in an antegrade direction. The secondary balloon 156, when sufficiently inflated, ensures that no retrograde blood flow occurs.

Similar to the configuration described in connection with FIG. 1A, the secondary inflation tube 148 defines a first lumen L1 configured to fluidly communicate with the inflation and deflation pump 150 and fluid reservoir. The secondary inflation tube 148 and/or the first lumen L1 may merge within the main secondary cannula 120 and continue to a fluid connection and communication with the secondary balloon 156. As with the structure of FIG. 1A, a second blood flow lumen, separated from the first lumen L1 is defined along and within the secondary cannula 120, extending from the CPB to the secondary balloon 156 and through the secondary balloon 156 to provide antegrade blood flow to the selected artery.

System 400 further comprises a suction catheter tube 402 with a region of suction 404 that may comprise a single opening, or a plurality of apertures, in fluid communication with a defined lumen extending through the suction catheter tube 402 which is, in turn, in operative communication with a return line of the CPB. In some embodiments, a suction pump may be provided which is in fluid communication with the lumen of the suction catheter tube 402 and with the return line of the CPB to help facilitate blood flow. The dashed lines of FIG. 4 indicate the possible connection options for the suction catheter tube 402. FIG. 5 illustrates the embodiment wherein the suction catheter tube 402 is directly connected with the CPB, without aid of an intervening suction pump.

An exemplary suction catheter tube 402 may comprise, without limitation, an exemplary 10 Fr (3.3 mm) shaft with an exemplary 20 Fr (6.7 mm) tip with an exemplary 20-30 holes in the tip to allow for suctioning of any blood coming back from the brain from the arch vessels that are not occluded. Other sizes will be readily apparent to the artisan and are within the scope of the present disclosure. As shown, the main cannula or catheter 102 is positioned within the aorta as described above, with the proximal side or end of the inflatable and deflatable descending aortic occlusion balloon 112, shown in an inflated configuration, positioned distal of the subclavian artery. The function and elements of the main cannula or catheter 102 of system 400 are the same as described above in connection with at least FIGS. 1A-1F.

With continued reference to FIGS. 1A-1F, FIGS. 6A and 6B illustrate a system 100' that is the same as the embodiments described above in connection with system 100, with the exception of the management of blood flow in the secondary cannula device. As illustrated, the antegrade blood flow from the CPB for both the main cannula tube 102 and for the secondary cannula device comprising the main secondary cannula tube 120 is achieved within the main cannula tube 102. A proximal region of the main secondary cannula tube 120 is located within the lumen 106 of the main cannula tube 102. At a point that is distal to the de-airing port 118, the main secondary cannula tube 120 exits from the main cannula tube and continues distally to connect fluidly connect with the manifold 128 as discussed above. A proximal end of the main secondary cannula tube may be fluidly connected with the CPB.

In other embodiments, the main secondary tube may fluidly connect though a port or aperture through the main cannula tube 102 with the descending aortic lumen 106 of the main cannula tube 102 which is, in turn, in fluidly connected with the CPB.

In some embodiments of system 100', as shown in FIG. 6B, two separate lumens defining two separate blood flow paths may be provided and defined within the main cannula tube 102 between the proximal opening 110 of the main cannula tube 102 and the fluid connection point between the main cannula tube 102 and the main secondary cannula tube 120, such that the fluid connection in this embodiment comprises a fluid connection between the main secondary blood flow lumen L4 of the main secondary cannula tube 120 and one of the two lumens defined within the proximal portion of the main cannula tube 102. The second of the two lumens defined within the proximal portion of the main cannula tube 102 will continue on to the distal opening 108 of the main cannula tube 102.

Exemplary Hemi-Arch Operative Embodiment

With reference to the Figures, and most specifically FIGS. 1A-1E, an exemplary hemi-arch operative embodiment will now be described. The ascending aorta and aortic arch may be accessed as per standing of care, e.g., a median sternotomy may be performed to access the mediastinum. The patient is placed on cardiopulmonary bypass per the surgeon's cannulation preference. For example, an aortic cannula may be placed in the aortic arch and a venous cannula in the right atrial appendage.

The patient's aorta may now be sized and the appropriate graft with a side-arm is selected and preloaded onto the back of the main body cannula 102. Alternatively, the sizing of the aorta, selection of the appropriate graft and/or preloading of the selected graft may be done later in the procedure, e.g., after placement of the main body catheter 102. An exemplary hemi-arch graft is shown in FIG. 1E. The illustrated graft comprises a substantially cylindrical hollow sleeve with two open ends and a branched side arm defining a lumen that fluidly communicates with the interior of the graft's hollow cylindrical sleeve as is well known in the art. The sleeve construction of the graft allows the surgeon to simply slide the graft over the main cannula and the secondary cannula in preparation for anastomosis.

A cannulation, e.g., a purse-string, suture may be used prior to placing a hollow needle that may be 18 gauge (though other sizes are within the scope of the present disclosure. A guidewire may be translated through the hollow needle and into the ascending aorta. The guidewire may be translated under echocardiographic guidance into the descending aorta. One or more dilators 107 may be used to gently enlarge the opening utilizing the well-known Seldinger technique.

The main body cannula 102 may be inserted over the guidewire into the descending aorta using the well-known over-the-wire translation technique. After confirming that the proximal side or end of the main descending aortic occlusion balloon 112 is translated distally beyond the subclavian artery and removal of the dilator 107, the arterial tubing from the CPB may be switched from the aortic cannula to the main body cannula 112. Determination of the position of the proximal side or end of the balloon 112 may be done using echocardiographic evidence and/or guided by a line marking the required distance to translate the balloon 112. Switching one of the A-lines of the arterial tubing of the CPB may be preceded by de-airing using the de-airing port 118 as is well understood in the art. The A-line is operatively connected with the proximal end of the main body cannula 112, placing the A-line in fluid communication with the main body cannula's descending aortic lumen 106. The patient is now on bypass using the above configuration as the arterial cannula. If another cannula was being used for arterial flow from the CPB, that cannula is disconnected and the corresponding arterial tubing clamped.

The descending aortic occlusion balloon 112 may, after it is positioned as above, be inflated in the descending aorta, ensuring perfusion of the lower body through the main body cannula 102 without backflow of blood into the surgical field.

After balloon inflation, the aneurysmal aorta is ready to be resected. The secondary cannula 130, 134, 138 may be inserted into arch vessel ostia and the associated secondary cannula balloons 142, 144, 146 inflated to allow antegrade perfusion of the brain without back flow. The secondary main cannula or tube 120 may, at its proximal end 122, be operatively connected to one of the A-lines and the secondary cannulas may be de-aired using the de-airing port 118.

The preloaded graft may be slid along the device to a position that is closer to, i.e., in proximity with, the resected aorta, in this scenario a hemi-arch, and the distal anastomosis completed.

Then the descending aortic occlusion balloon 112 may be deflated followed by deflating of the secondary balloons 142, 144, 146.

The main body catheter 102 and secondary cannula or tube 120 including the secondary cannulas 130, 134, 138 and associated structures may now be removed, and the arterial tubing switched over to the sidearm of the aortic graft.

The aortic graft may now be cross-clamped and the proximal anastomosis conducted.

Significantly, this operation may be conducted at mild hypothermia to normothermia, or other temperatures, as described above.

Alternative Exemplary Operative Methodology Embodiment

Another operative method is now described generally with reference to FIGS. 1A-5, and with more specific reference to FIGS. 4 and 5, the initial steps of which are the same as described above regarding the hemi-arch procedure. Thus, the ascending aorta and aortic arch may be accessed as per standard of care (median sternotomy or other minimally invasive methods). The arterial line from the CPB may be y-ed twice prior to hooking up the circuit. A cannulation purse-string stitch may be placed in the ascending aorta. Then an exemplary 18-gauge hollow needle may be used to access the aorta in the middle of this purse-string suture. Then a guidewire may be placed through the hollow needle under echocardiographic guidance and extended into the descending aorta. A set of dilators may be used to enlarge the aortic insertion point utilizing Seldinger technique. The main cannula tube 102 may be inserted into this point over the wire. The main cannula tube 102 and descending aortic occlusion balloon 112 may be inserted and translated over-the-wire until the proximal end of the balloon 112 is confirmed to be distal to the left subclavian artery under echocardiographic evidence and/or as also guided by a line of known length. At this point (or later as described supra), the aortic arch may be measured to size for the graft and the graft with a sidearm may be loaded onto the back end of the device.

Then the arterial tubing of the CPB may be connected to a proximal end 110 of the main body catheter 102, using the de-airing portal 118 as needed. Now the patient is on bypass using both this circuit and the innominate/axillary artery cannula as their arterial perfusion. The secondary cannula tube 120 may be operatively connected to the arterial tubing of the CPB and the cannula may be de-aired and clamped to be ready to be inserted once the aorta is resected.

A suction catheter tube 402 with a suction portion 404 on or near a distal end of the suction catheter tube 402 may be connected with a return or V-line of the CPB. As described above in connection with FIGS. 4 and 5, a suction pump may be connected between the suction catheter tube 402 and the CPB in an alternate configuration. The suction portion 404 may be positioned within the aortic arch and proximal to the arch vessels that are not occupied by the main secondary catheter 120 and associated balloon 148. The descending aortic balloon 112 may be inflated. Then the aorta may be resected as indicated around the inserted device(s). Direct access is now provided to the arch vessels at which point, the secondary cannula may be inserted into the left common carotid artery or left subclavian artery and undamped.

The secondary cannula balloon 156 may then be inflated. The pre-loaded graft may, as discussed above, be brought closer to the resected aortic end and the distal anastomosis conducted with the device in the lumen. Once the anastomosis is completed, the main body balloon 112 may be deflated and the relevant arterial tubing switched to the sidearm of the aortic graft. The secondary cannula balloon 156 may also be deflated and removed with the main cannula tube 102 after de-airing of the graft is completed. A cross-clamp may be placed on the aortic graft and the rest of the operation conducted as indicated. This operation could be conducted at mild hypothermia to normothermia, or other temperatures, as described above.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

I claim:

1. A kit for perfusing one or more arteries of a patient, the kit comprising:

- a main cannula tube having a proximal portion, a distal portion configured to be positioned in the patient's descending aorta, and a main perfusion lumen extending through the main cannula tube, wherein the proximal portion of the main cannula tube is configured to be fluidly coupled to a cardiopulmonary bypass machine ("CPB") to provide blood flow through the main perfusion lumen;
- a main occlusion element surrounding the distal portion of the main cannula tube such that the main perfusion lumen remains patent when the occlusion element is expanded;
- a secondary cannula tube having a proximal portion configured to be fluidly coupled to the CPB, a distal portion configured to be positioned in one of the innominate artery, the left carotid artery, or the left subclavian artery of the patient, and a secondary perfusion lumen extending through the secondary cannula tube; and
- a secondary occlusion element at the distal portion of the secondary cannula tube.

2. The kit of claim 1, wherein the main occlusion element is a balloon.

3. The kit of claim 1, wherein the secondary occlusion element is a balloon.

4. The kit of claim 1, further comprising a graft pre-loaded over the main cannula tube.

5. The kit of claim 4, wherein the graft is a hemi-arch graft.

6. The kit of claim 1, wherein the secondary cannula tube is a first secondary cannula tube and the artery is a first artery, and the kit further comprises:

- a second secondary cannula tube configured to be positioned in a second artery of the patient, the second artery being another one of the innominate artery, the left carotid artery, or the left subclavian artery, wherein the second secondary cannula tube has a second secondary perfusion lumen, a second secondary occlusion element at a distal region, and a proximal end configured to be fluidly coupled to the CPB, and wherein the second secondary cannula tube is configured to be positioned such that a distal end of the second secondary perfusion lumen is located distally beyond the second secondary occlusion element.

7. The kit of claim 6, further comprising:

- a third secondary cannula tube configured to be positioned in a third artery of the patient, the third artery being another one of the innominate artery, the left carotid artery, or the left subclavian artery, wherein the third secondary cannula tube has a third secondary perfusion lumen, a third secondary occlusion element at a distal region, and a proximal end configured to be fluidly coupled to the CPB, and wherein the third secondary cannula tube is configured to be positioned such that a distal end of the third secondary perfusion lumen is located distally beyond the third secondary occlusion element.

8. The kit of claim 1, further comprising an expandable stent configured to be positioned in the thoracic aorta and operatively coupled to the main occlusion element, wherein the expandable stent is configured to be in a collapsed configuration when the main occlusion element is in a deflated state, and wherein the expandable stent is configured to be in an expanded configuration when the main occlusion element is in an inflated state.

9. The kit of claim 1, further comprising an embolic protection device distal of the secondary occlusion element.

10. The kit of claim 1, wherein, when the main perfusion lumen is fluidly coupled to and receiving blood from the CPB, the main perfusion lumen provides sufficient blood flow to the lower body to meet metabolic needs at operative bodily temperatures.

11. The kit of claim 1, wherein the secondary occlusion element surrounds the distal portion of the secondary cannula tube.

* * * * *